(12) United States Patent
Jordan

(10) Patent No.: US 6,985,769 B2
(45) Date of Patent: Jan. 10, 2006

(54) AUTOMATED REALTIME INTERPRETATION OF BRAIN WAVES

(75) Inventor: Kenneth George Jordan, Riverside, CA (US)

(73) Assignee: Jordan Neuroscience, Inc., San Bernadino, CA (US)

( * ) Notice: Subject to any disclaimer, the term of this patent is extended or adjusted under 35 U.S.C. 154(b) by 77 days.

(21) Appl. No.: 10/468,052

(22) PCT Filed: Feb. 13, 2002

(86) PCT No.: PCT/US02/04807

§ 371 (c)(1),
(2), (4) Date: Aug. 12, 2003

(87) PCT Pub. No.: WO02/064024

PCT Pub. Date: Aug. 22, 2002

(65) Prior Publication Data

US 2004/0077967 A1    Apr. 22, 2004

Related U.S. Application Data

(60) Provisional application No. 60/268,388, filed on Feb. 13, 2001.

(51) Int. Cl.
A61B 5/04    (2006.01)

(52) U.S. Cl. ..................................... 600/544

(58) Field of Classification Search ................ 600/544, 600/545

See application file for complete search history.

(56) References Cited

U.S. PATENT DOCUMENTS

| 4,188,956 | A |   | 2/1980  | John ........................... 600/544 |
| 4,736,307 | A |   | 4/1988  | Salb ........................... 600/544 |
| 4,857,716 | A | * | 8/1989  | Gombrich et al. ........... 235/375 |
| 4,862,359 | A |   | 8/1989  | Trivedi et al. .............. 600/544 |
| 4,928,704 | A |   | 5/1990  | Hardt .......................... 600/545 |
| 5,010,891 | A | * | 4/1991  | Chamoun ................... 600/544 |
| 5,020,540 | A |   | 6/1991  | Chamoun ................... 600/509 |
| 5,047,930 | A |   | 9/1991  | Martens et al. ............. 600/509 |
| 5,218,530 | A |   | 6/1993  | Jastrzebski et al. ......... 382/207 |
| 5,230,346 | A |   | 7/1993  | Leuchter et al. ............ 600/544 |
| 5,299,118 | A |   | 3/1994  | Martens et al. ............. 600/509 |
| 5,601,088 | A |   | 2/1997  | Swanson et al. ............ 600/510 |
| 5,630,425 | A |   | 5/1997  | Panescu et al. ............. 600/508 |
| 6,052,619 | A |   | 4/2000  | John ........................... 600/544 |
| 6,097,980 | A |   | 8/2000  | Monastra et al. ........... 600/544 |
| 6,434,419 | B1| * | 8/2002  | Gevins et al. .............. 600/544 |
| 6,496,724 | B1| * | 12/2002 | Levendowski et al. ..... 600/544 |

* cited by examiner

*Primary Examiner*—Robert Nasser
*Assistant Examiner*—Navin Natnithithadha
(74) *Attorney, Agent, or Firm*—Robert J. Rose; Michael Fedrick; Sheldon & Mak

(57) ABSTRACT

A method and system for automated real time interpretation of brain waves in an acute brain injury of a patient using correlations between brain wave frequency power ratio and wave morphology, determined by a measure of the rhythmicity and variability of the brain wave as a function of the slope of the brain wave upstroke, the arc of the brain wave, and the synchronicity of the brain wave. A system is provided with a central processing unit (16), an electroencephalogram acquisition unit (18), a reference database (24), a quantitative electroencephalogram analysis program (14), and a display device (26) for communicating the classification of the acquired electroencephalographic signals. Artifact rejection is also provided.

20 Claims, 11 Drawing Sheets

AUTOMATED REALTIME INTERPRETATION OF BRAIN WAVES

CROSS-REFERENCE TO RELATED APPLICATIONS

This Application claims priority from International Application Number PCT/US02/04807, titled "Automated Realtime Interpretation of Brain Waves," filed Feb. 13, 2002, and from U.S. provisional application Ser. No. 60/268,388, titled "A System For Automated Realtime Interpretation Of Brain Waves In Acute Brain Injuries," filed Feb. 13, 2001.

BACKGROUND

Acute brain injuries ("ABI") due to trauma, stroke, seizures, hypoxia, and infections affect more than 10 million Americans annually. They are a leading cause of death and disability, and cost society over $60 billion dollars annually. A major reason for poor outcomes from ABIs is the "secondary injury" to the brain. This term refers to potentially preventable brain damage that is added to and complicates the original or "primary" injury. Secondary injury is usually due to insufficient oxygen or circulation to the brain to meet its demands. This can be caused by upper airway obstruction, blood loss, hypotension, brain swelling (cerebral edema), seizures, delayed cerebral hemorrhage, and increased intracranial pressure, among others. Brain injury is exquisitely time dependent. Even brief delays of a few minutes in preventing or reversing secondary brain injury may result in permanent and fatal damage. A device, which rapidly detects, monitors and communicates the real-time and dynamic condition of brain function during an ABI could markedly improve the timeliness and appropriateness of corrective intervention. Having this information immediately available where the victim is first triaged and stabilized, which is usually in the field by paramedic-emergency medical technologists, would minimize any delay in corrective and preventive intervention.

The heart and the brain are the two largest electricity-generating organs in the body and the two most critical to survival in acute injuries. For more than forty years in acute cardiac injury the EKG has been a standard of care, serving the diagnostic and monitoring functions described above. In ABI, however, no equivalent tool has been established. The most logical candidate is the EEG (electroencephalogram), which has been available for decades as a routine. method for diagnosing normal and abnormal brainwave activity in chronic diseases. In spite of striking similarities between the EKG and EEG in their electrophysiology, methodology, and clinical utility, the EEG, unlike the EKG, has never been systematically applied to acute injuries. The main reason for this omission is, traditionally, that EEG has been perceived as a complex and highly sophisticated procedure, which requires specially trained experts to set up, run and interpret a study. These experts are not readily available in emergency settings, particularly at the scene of ABIs in the field. In addition, unlike the case with EKG testing, emergency medical, paramedical, and allied health professionals who attend victims of ABIs are not trained in EEG set-up or interpretation, nor are these considered within their usual scope of practice.

A method for using computerized telecommunication technology with real-time interpretation by one or more remote EEG expert readers may help, but does not fully solve this problem. It would be beneficial for an emergency team to have equipment on site that, like modern computerized EKG machines, rapidly performs a brainwave test and automatically determines if the brain function is normal or abnormal, as well as provide simple and reliable key diagnostic information.

What is needed is a "self-interpreting" EEG unit, which can be set-up to acquire brainwaves by non-experts at the ABI site, and provide rapid automated interpretation in clinically meaningful terminology.

SUMMARY

The present invention provides accurate, reliable, and simple real-time acquisition and interpretation of brainwaves in acute brain injuries at the site of the victims. The present invention provides this interpretation automatically according to a simple and clinically relevant algorithm, and independently of expert interpreters of brain waves. The present invention communicates this automatic interpretation to non-experts at the site of the victim by an unambiguous signal, or a set or series of signals, which will facilitate onsite rapid and appropriate medical decisions and treatment.

A method for automated real time interpretation of brain waves in an acute brain injury of a patient is described using a correlation between brain wave frequency power ratio and wave morphology. The power ratio may be an alpha-beta/theta-delta power ratio. Various methods of determining wave morphology are disclosed including a measure of the rhythmicity and variability of the brain wave as a function of the slope of the brain wave upstroke, the area of the brain wave, and the synchronicity of the brain wave.

A method for automated real time interpretation of brain waves in an acute brain injury of a patient is described comprising the steps of acquiring electroencephalographic signals from the patient, selecting one or more than one of the acquired electroencephalographic signal for analysis, transforming the one or more than one selected electroencephalographic signal into one or more than one frequency component, calculating a power ratio for each of the one or more than one selected electroencephalographic signal, accessing a reference database storing reference power ratios calculated from normal brain wave activity data, comparing the one or more than one calculated power ratio to the reference power ratios to determine whether the one or more than one calculated power ratio is abnormally high or low, interpreting the one or more than one selected electroencephalographic signal based upon the comparison of the one or more than one calculated power ratio to the reference power ratios, and communicating the interpretation of the selected electroencephalographic signals as the interpretation of the acquired electroencephalographic signals. In a further embodiment the method includes the step of measuring the wave morphology of the one or more than one selected electroencephalographic signal, and the interpreting step further comprises consideration of the measured wave morphology.

In a still further embodiment, the reference database further comprises classification data correlating acute brain injury electroencephalographic categories with specific types of brain dysfunction, and the method further comprises the step of classifying the one or more than one compared power ratio into one or more than one of the acute brain injury electroencephalographic categories, and the communicating step further comprises communicating the classification.

In further embodiments, the step of comparing further comprises determining the spatial distribution of any abnormality, and the communicating step further comprises displaying a quadrant schematic representation for communicating the interpretation of the electroencephalographic signals.

A method for automated real time interpretation of brain waves in an acute brain injury of a patient is described comprising the steps of, under the control of a user system, connecting one or more than one electroencephalogram needle electrode of an electroencephalogram acquisition unit to the patient, activating the electroencephalogram acquisition unit and transmitting digital electroencephalographic signals from the patient to the electroencephalogram acquisition unit, and receiving a display of the electroencephalogram of the patient connected to the electroencephalogram acquisition unit and information automatically interpreting the meaning of the display. In a further embodiment the receiving step further comprises receiving a display illustrating a quadrant schematic representation of the interpretation of the electroencephalographic signals.

In still further embodiments, the method further comprises the steps of receiving information displaying the position of one or more than one electroencephalogram needle electrode connected to the patient, receiving a request to alter the position of one or more than one electroencephalogram needle electrode connected to the patient, requesting demographic data relating to the connected patient, requesting clinical information about the connected patient's condition, medications, and other relevant medical information required for clinical correlation of electroencephalogram data, or scanning bar-coded data having information regarding the patient connected to the electroencephalogram acquisition unit.

A system for automated real time interpretation of brain waves in acute brain injuries in a patient is described comprising a central processing unit, an electroencephalogram acquisition unit coupled to the central processing unit having a first port for receiving electroencephalographic signals, a reference database coupled to the central processing unit for storing one or more than one reference power ratio calculated from normal brain wave activity, a first memory coupled to the central processing unit for storing a quantitative electroencephalogram analysis program, the quantitative electroencephalogram analysis program comprising a transform module for transforming acquired electroencephalographic signals into frequency components, a calculation module for calculating a power ratio from the frequency components, a classification module for comparing the calculated power ratio to reference data and classifying the acquired electroencephalographic signals; and a display device for communicating the classification of the acquired electroencephalographic signals.

In a further embodiment the reference database further comprises classification data correlating acute brain injury electroencephalographic categories with specific types of brain dysfunction, the classification module is further for classifying the calculated power ratio into one or more than one of the acute brain injury electroencephalographic categories, and the display device is further for communicating the classification. In a further embodiment the classification module is an artificial neural network.

A second memory coupled to the central processing unit may be added for storing an artifact pattern recognition program for minimizing artifact contamination of received digital electroencephalographic signals. The calculation module may also calculate rhythmicity and variability of the brain wave as a function of the slope of the brain wave upstroke, the area of the brain wave, and the synchronicity of the brain wave.

BRIEF DESCRIPTION OF DRAWINGS

These and other features, aspects, and advantages of the present invention will become better understood with reference to the following description, appended claims, and accompanying drawings, where:

DETAILED DESCRIPTION

The present invention is directed to a system and method for automated real time interpretation of brain waves in acute brain injuries ("ABI"). In one embodiment of the invention electroencephalogram ("EEG") signals acquired from an EEG acquisition unit ("EEG AU") are quantitatively analyzed and automatically interpreted into clinically meaningful terminology. In an emergency setting, this can be referred to as an Automated Emergency EEG System (AutoEEG). The invention can also be named according to the ABI site in which it is used, such as ER-EEG AU, ICU-EEG AU, and EMS (emergency medical system)-EEG AU. In one embodiment, the AutoEEG machine using the present invention can be used by non-experts, including ER technicians, nurses, paramedics, ICU nurses, nurses' aides, among others who are personally attending patients with ABI at or near the sites of their injuries. No training other than that received through the AutoEEG training method should be necessary to operate the AutoEEG. Preferably, the AutoEEG runs digital EEG software modified to present simplified, friendly and engaging interfaces to the operator, and optionally with automatic cueing windows to instruct the operator in basic terms through each sequential step.

Figure 1:
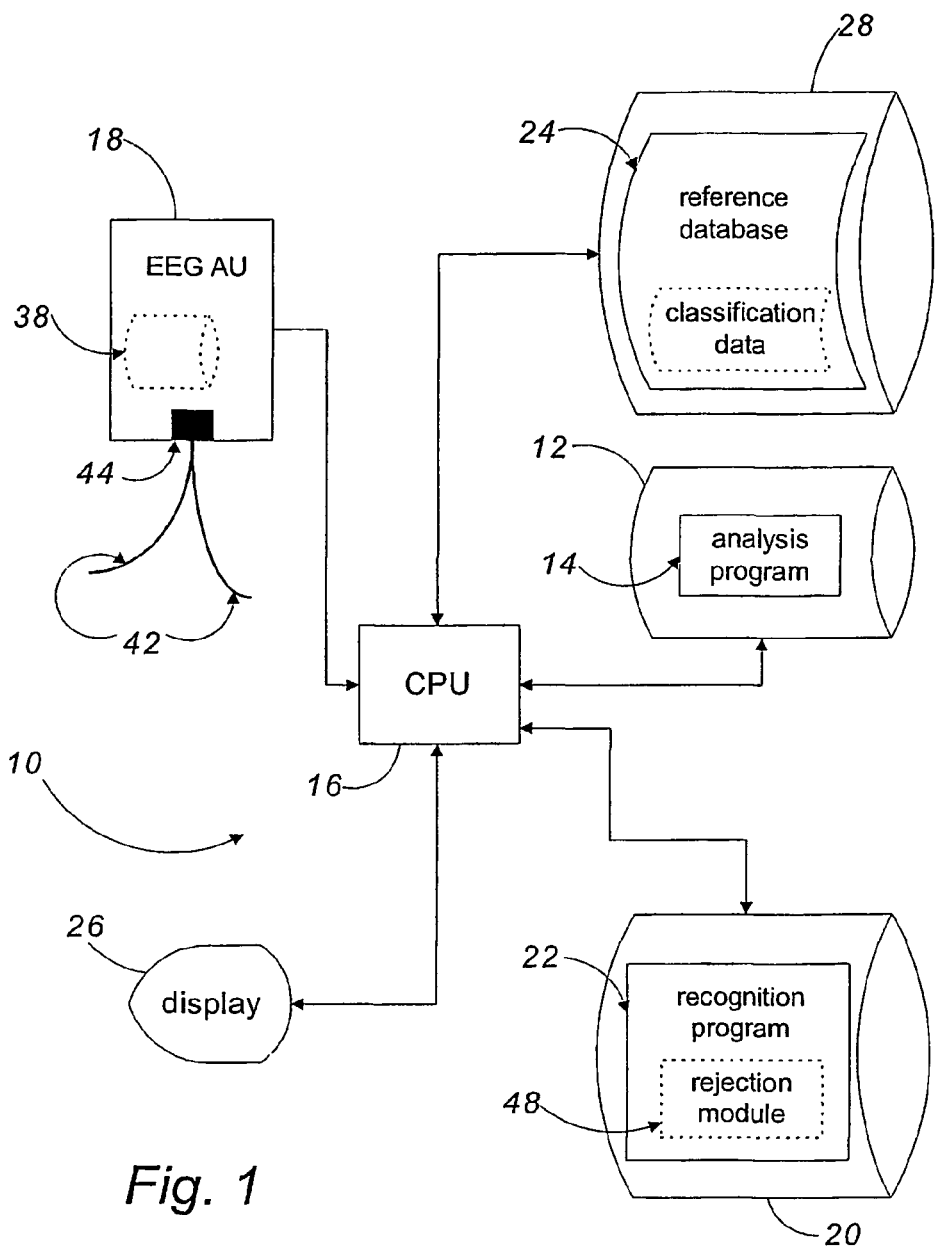
FIG. 1 is a system diagram of the system for automated real time interpretation of brain waves according to the present invention.

FIG. 1 illustrates one embodiment of an automated emergency EEG system (AutoEEG) 10 useable in implementing a method for automated real time interpretation of brain waves in acute brain injuries. The system comprises an automated electroencephalogram acquisition unit 18 (EEG AU) coupled to a central processing unit 16, a first memory 12 coupled to the central processing unit 16 for storing a quantitative electroencephalogram analysis program 14, a second memory 20 coupled to the central processing unit 16 for storing an artifact pattern recognition program 22 for minimizing artifact contamination of received digital electroencephalographic signals, a third memory 28 coupled to the central processing unit 16, for storing a reference database 24 comprising one or more than one reference power ratio calculated from normal brain wave activity, and a display device 26 coupled to the central processing unit 16 for displaying the output of the analysis program. Optionally, in a further embodiment of the invention, the reference database 24 further comprises classification data for storing acute brain injury electroencephalographic categories having established correlations with specific types of brain dysfunction, and correlations of wave morphology and power ratios to specific brain dysfunction.

The requirements for the CPU 16 can vary as the surrounding physical environment dictates. For example, a CPU located in an ER or an ICU would not have to be contained in a portable unit, while a CPU used in field situations should be contained in an enclosure that is durable, sturdy, portable, and stable. A standard Pentium®-type or Macintosh®-type personal computer with an adequate hard drive, RAM, processing speed and input ports would be able to operate the needed AutoEEG software. The three memories can be separated, or combined.

Referring to FIG. 1, the EEG AU 18 includes a first port interface 44 for attaching EEG needle electrodes 42. EEG needle electrodes 42 are connected to a patient and attached to the first port interface 44 of the EEG AU 18. The EEG needle electrodes 42 transmit brain wave activity of the patient as digital electroencephalographic signals (DEEG signals) 46, shown on FIG. 3. As the EEG AU 18 acquires the digital electroencephalographic DEEG signals 46, they are recorded and quantitatively analyzed in real time as explained below.

Figure 3:
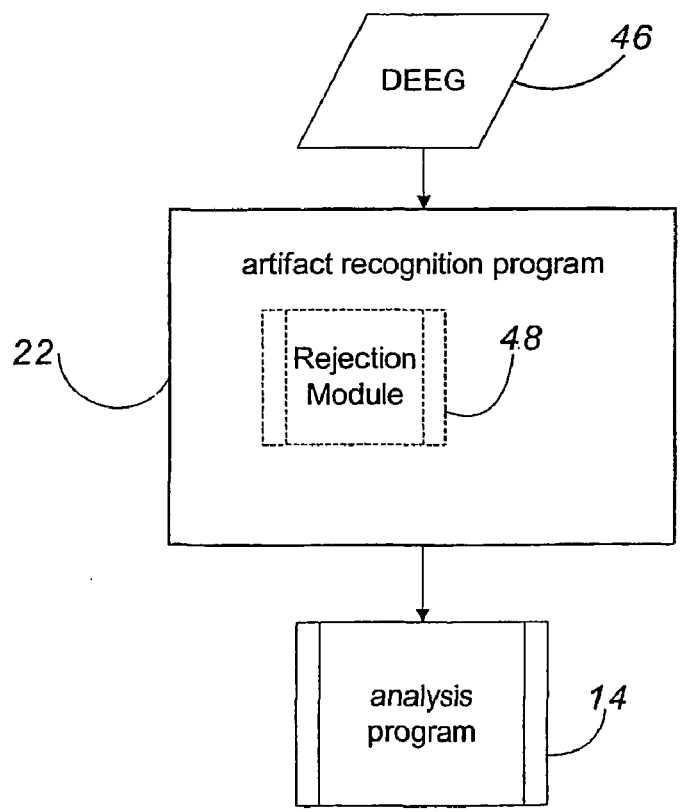
FIG. 3 is a flow diagram of a method for automated real time interpretation of brain waves in an acute brain injury of a patient.

Referring to FIG. 3, the acquired DEEG signals 46 are first processed by the artifact recognition program 22, which is stored in the second memory 20, to minimize contamination by artifacts. The DEEG signals 46 are then passed to the EEG analysis program 14 which transforms the DEEG signals 46 into frequency and amplitude measurements, or power (amplitude squared) measurements, derived from a mathematical formula for wave subgroup analysis called the Fast Fourier Transform (FFT), and then analyzes the signals as disclosed herein. The application of the FFT is well known to those skilled in the art with reference to this disclosure.

In a further embodiment, it is possible for real-time quantitative EEG (QEEG) signals to be generated as the EEG AU 18 records the raw DEEG signals 46. Unlike conventional application of the FFT for QEEG, the AutoEEG System 10 of FIG. 1 does not have to rely upon post hoc reader selection of EEG epochs for analysis. Instead, the AutoEEG System 10 can use a real-time rejection module 48 to eliminate epochs from analysis with excessive noise. Various methods to select out epochs with excessive noise will be evident to those skilled in the art with reference to this disclosure, preferably by incorporating the rejection module 48 within artifact pattern recognition program 22. One preferred method for implementation of a rejection module 48 uses artifact pattern recognition, or what may be called artifact rejection technology (ART). ART as implemented within the artifact pattern recognition program 22 (APR) recognizes waveforms resulting from muscle movement, and other artifacts, and minimizes them from contaminating the QEEG record.

In addition, the AutoEEG System 10 can easily be modified to analyze epochs of 30 seconds to 2 minutes in duration rather than the conventional 10–20 minutes duration. This allows for faster analysis and results in display in real time or "near" real time speed. The AutoEEG System 10 can analyze a received epoch at the same time it is receiving the next epoch. The resulting calculation of component waves can be displayed on a display device 26 in a variety of formats to assist meaningful and simplified communication of otherwise cryptic and confusing raw EEG data to the non-expert. Display options include bar graphs, compressed spectral array, and topographic scalp maps.

In an alternative embodiment, the artifact pattern recognition program 22 is contained within the EEG AU 18, thereby reducing computing load on the CPU 16.

Various formulae and ratios of EEG frequency spectral bands show good correlation with established clinical conditions, as is known in the art with reference to this disclosure. For example, the ratio of alpha (8–13 Hz) power to theta (4–7 Hz) plus delta (0.5–3 Hz) power is a sensitive indicator of cerebral ischemia. In an ischemic brain injury such as a stroke, the alpha power is abnormally decreased and the theta-delta power is abnormally increased. Alterations of total power, percentage alpha and percentage delta of total EEG correlate with acute stroke injuries. A measure of the spontaneous variability of alpha frequency called, "percent alpha variability," is an early measure of evolving cerebral ischemia after subarachnoid hemorrhage and trauma, called vasospasm. Measures of coherence and rhytimicity and automated epileptiform and seizure detection algorithms are other QEEG functions which have potential application to the purposes of the invention.

There are other programs and strategies available for the quantitative analysis of EEG activity which may in alternative embodiments be applied to the purposes of the invention. These programs and strategies include, but are not limited to adaptive segmentation with feature clustering, "rule-based" spike and seizure detection algorithms, adaptive-filtering methods for pattern recognition, and time-frequency distribution analysis. By applying these rules through the EEG analysis program 14, it is therefore possible to provide rapid automated interpretation in clinically meaningful terminology, useable by non-experts at the ABI site.

Figure 2:
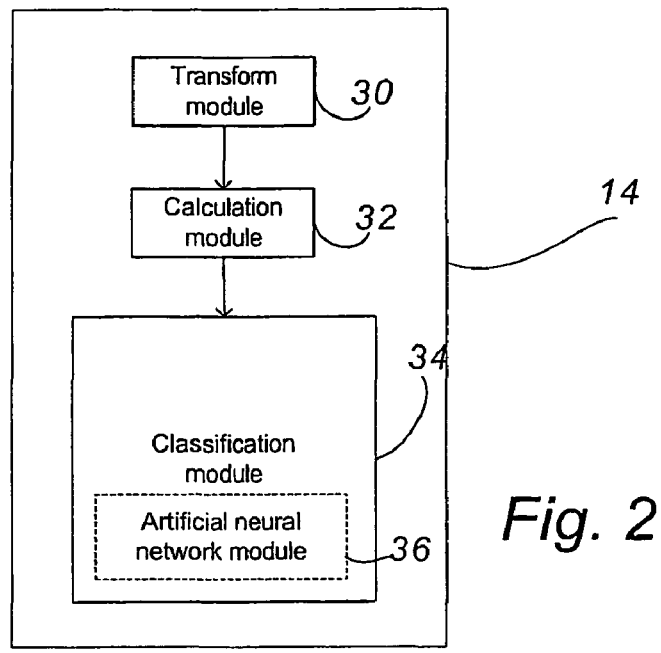
FIG. 2 is a component diagram of a quantitative electroencephalogram analysis program useable in the system of FIG. 1.

In a preferred embodiment, the quantitative EEG analysis program 14 stratifies and analyzes spectral frequency bands of real-time EEG recorded from the EEG AU 18 and also analyzes the percent alpha variability and wave rhythmicity. Various methods can be used. Referring to FIG. 2, in one embodiment the quantitative EEG analysis program 14 comprises a transform module 30 for transforming acquired signals using FFT technology, a calculation module 32 for calculating power ratios, and in a further embodiment, for calculating wave morphology based on rhythmicity and variability of the brain wave, as a function of the slope of the brain wave upstroke, the area of the brain wave, and the synchronicity of the brain wave, and a classification module 34 for comparing power ratios, and in a further embodiment rhythmicity and variability, and classifying the signals. In a still further embodiment the classification module further comprises an artificial neural network module 36.

Referring to FIGS. 2 and 3, selected EEG epochs are screened and passed by the artifact pattern recognition program module 22 to the transform module 30 of the quantitative electroencephalogram analysis program 14. The transform module 30 transforms the acquired digital electroencephalographic signals into one or more than one frequency component, using the FFT. It should be noted that while it is possible to dispense with processing by the artifact recognition program 22, such processing before application of the FFT should yield far better results.

The calculation module 32 then calculates an alpha-beta/theta-delta power ratio for each of one or more than one frequency component. The classification module 34 then compares one or more than one calculated alpha-beta/theta-delta power ratio to one or more than one reference power ratios stored in the reference database 24 and recognizes if 1) the ratio is normal or abnormal high or low, and 2) the spatial distribution of the ratio. An abnormally high alpha-beta/theta-delta power ratio has been found to correlate well with a seizure. A low alpha-beta/theta delta power ratio has been found to correlate well with an area of structural injury, such as a stroke or mass lesion. The spatial distribution determines if it is a focal or diffuse process, and can be determined by repeating the foregoing analysis for each topographic quadrant of the brain.

Figure 5:
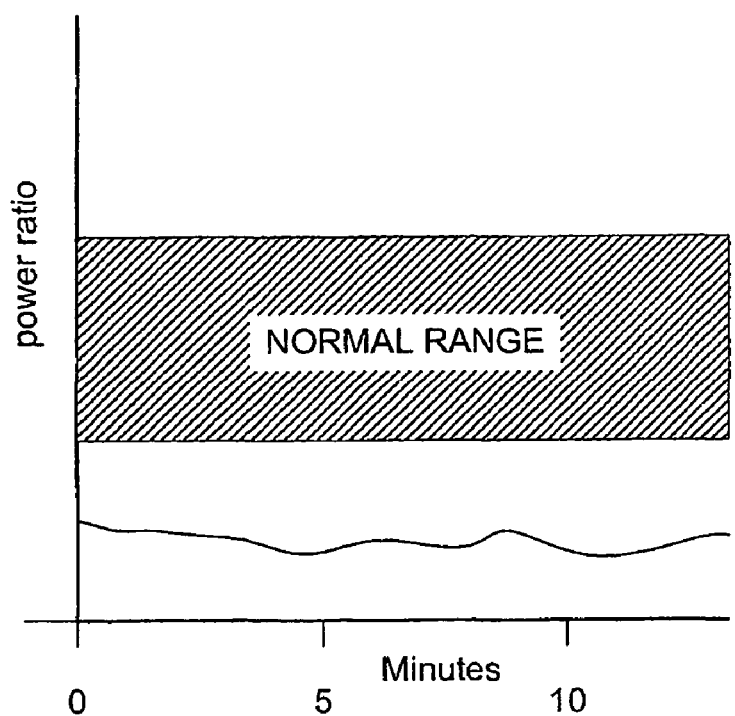
FIG. 5 is a sample AutoEEG real time single function QEEG plot.

FIG. 5 is a sample AutoEEG real time single function QEEG plot for the left frontal quadrant in acute left frontal stroke. The power ratio function is used to identify and display abnormally decreased faster frequencies (alpha-beta) and increased lower frequencies (theta-delta) in a localized brain region. The sample plot shows an abnormally low ratio, a focal low/slow pattern, which is a characteristic pattern of structural brain injuries, such as strokes, trauma and hemorrhages.

Figure 6:
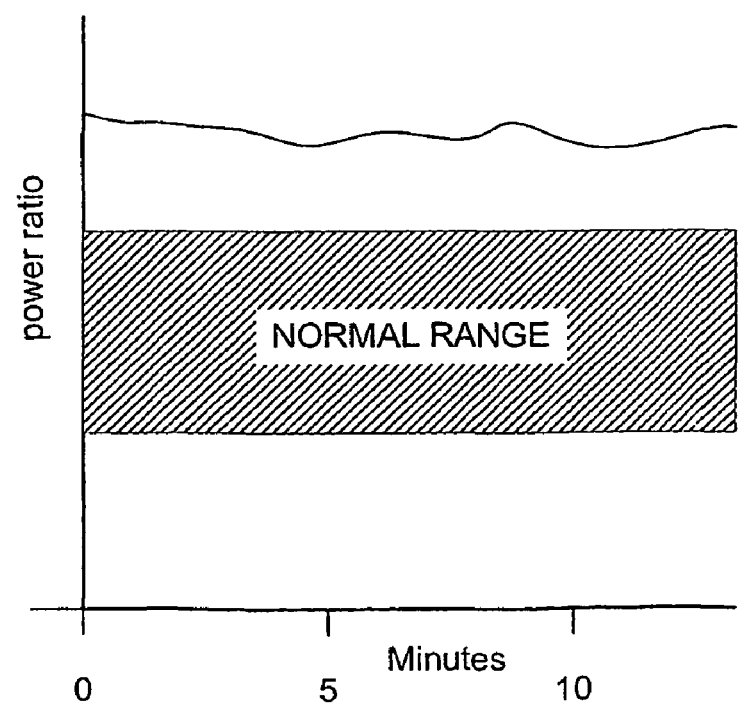
FIG. 6 is a sample AutoEEG real time single function QEEG plot.

FIG. 6 is a sample AutoEEG real time single function QEEG plot for the left frontal quadrant in acute left frontal seizure. The power ratio function is again used to identify and display abnormally increased power of fast frequencies (alpha-beta). The sample plot shows an abnormally high ratio, a focal seizure pattern, which is a characteristic electroencephalographic marker of ictal (seizure) activity. If the corresponding plots for the other brain quadrants were within or closer to normal range, this plot would indicate that the seizure activity is occurring in the left frontal region.

The use of the power ratio therefore acts as an indicator that can be used in the analysis program 14 to yield interpretations that can be displayed to the user. Various embodiments of the power ratio can be used, such as alpha/theta-delta, in addition to alpha-beta/theta-delta.

Figure 7:
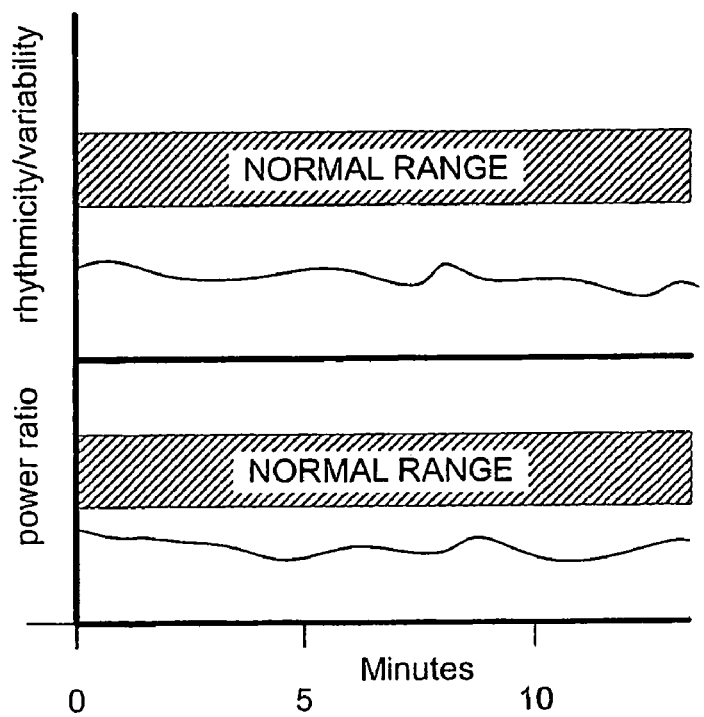
FIG. 7 is a sample real time dual function QEEG plot.

Optionally in a different embodiment, a second function can be correlated against the power ratio (whichever embodiment is used) in order to increase sensitivity and/or specificity of the derived QEEG. FIG. 7 is a sample real time dual function QEEG plot in which a function that quantifies wave morphology by rhythmicity and variability, is displayed simultaneously with the power ratio. Wave morphology may be measured by several methods, including the consistency of the slope of upstroke and downstroke of each wave (ascending and descending time constants), and the reproducibility and simultaneity of wave morphology (predictability and coherence).

Quantification of wave morphology can be accomplished in a variety of ways, each having the characteristic that high rhythmicity-low variability is consistent with seizure, and low rhythmicity-high variability is consistent with stroke or other structural lesion. One quantification scheme is demonstrated in FIG. 8, in which the slope of the upstroke is plotted against the wave area for a wave pattern that is synchronous in all channels analyzed. Quantitatively, the slope of the upstroke may be found from the derivative of the EEG signal, and the wave area may be found from the integration of the signal. Four distinct quadrants may be considered, as shown on FIG. 8.

Quadrant I, the upper left quadrant, represents a rapidly rising upstroke associated with a small wave area. This would be the pattern for sharp waves or spikes, which if synchronous, indicates a seizure.

Quadrant IV, the lower right quadrant, represents a slowly rising upstroke associated with a large wave area. This would be the pattern for larger, gradual waves, which if synchronous, indicates a toxic or metabolic abnormality.

Quadrant III, the lower left quadrant, represents a slowly rising upstroke associated with a small wave area. This would be the pattern for smaller, gradual waves, which if synchronous, indicates either normal activity or a possible medication effect.

Quadrant II, the upper right quadrant, represents a rapidly rising upstroke associated with a large wave area. This would be a pattern consistent with artifacts.

Figure 8:
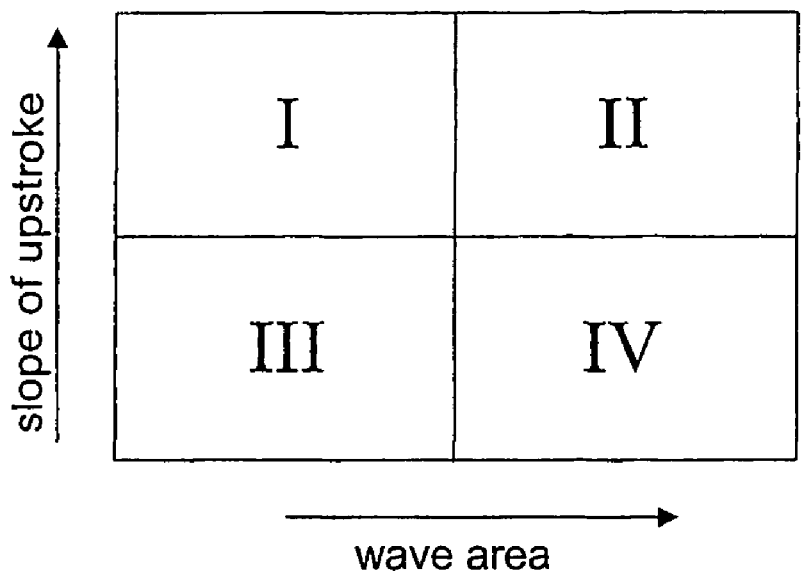
FIG. 8 is an x-y plot of wave area versus slope of upstroke.
Figure 9:
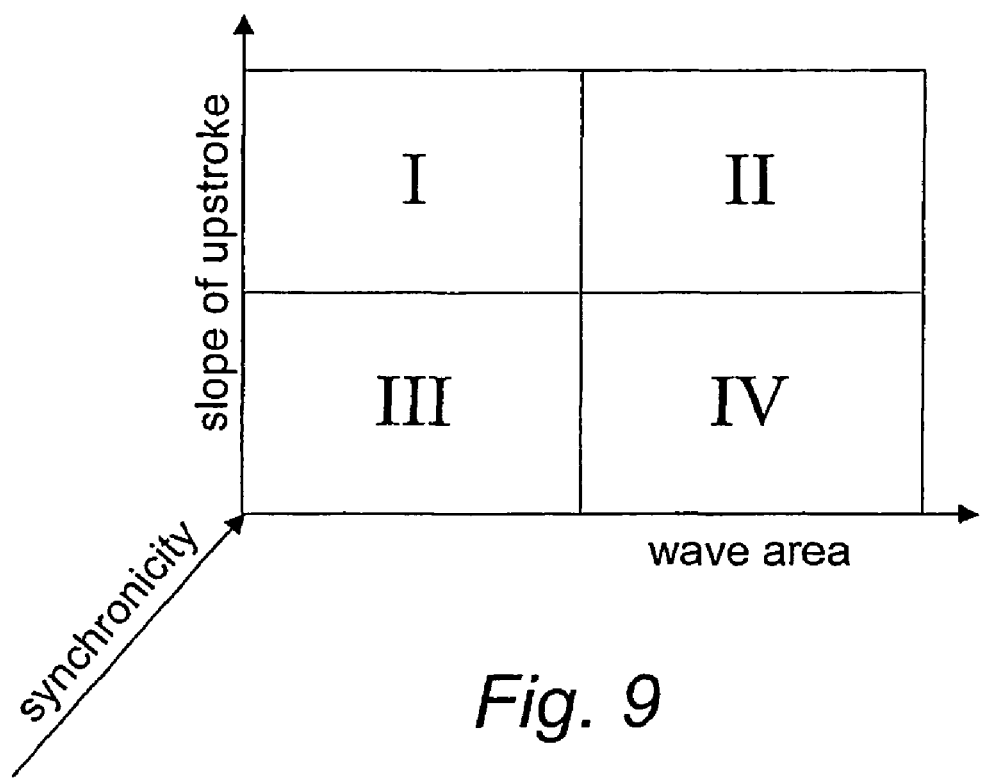
FIG. 9 is a 3D plot of the x-y plot of FIG. 8 versus synchronicity on an inverted z-axis.

As noted, the correlation of FIG. 8 is for synchronous wave activity, that is waves that are simultaneously present in similar morphology in a plurality of channels of the EEG. The analysis program can compare the signal from each channel, comparing the slope (e.g., derivative) and area (e.g., integral), and arrive at a measure of the degree of synchronicity of the wave being analyzed. As shown in FIG. 9, this can represent a third axis of correlation, which is inverse plotted (high synchronicity is near the slope-area axis) for ease of interpretation.

A function may then be created dependent upon the three variables of slope, area, and synchronicity, which yields a value for rhythmicity/variability. High rhythmicity/variability is associated with values in Quadrant I close to the slope-area axis, that is high slope, small area, high synchronicity. Low rhythmicity/variability is associated with values closer to Quadrant IV and further from the area-slope axis. Any construct for the rhythmicity/variability function will work which has this characteristic.

While it is possible to perform the analysis of wave morphology using signal processing methods as just described, in a further embodiment an artificial neural network module 36 classifies one or more than one compared alpha-beta/theta-delta power ratio into normal or specified abnormal categories. The artificial neural network module is trained for the purpose of recognizing and distributing the frequency ratios into normal or specified abnormal categories.

Preferably, a visually displayed scalp map of electrode positions signals by superimposed images, colors, or other indicia, the nature and location of the QEEG analysis. For example, if there is an area of abnormally reduced ratio in the left frontal area of the patient's brain, the left frontal segment of the scalp map assumes a distinctive color. This is accompanied by distinctive audible and textual signals to the operator. In a further embodiment, indicia may indicate the confidence of the category. For example, the distinctive color on the scalp map might assume varying intensity.

In one embodiment of the invention, a novel "AutoEEG Classification System" (AECS) sorts the multiplicity of EEG patterns recognized by one or more of the above methods into one or a combination of a few AECS categories.

An example of categories that may be used is included but not limited to the categories listed in Table 1 below.

TABLE 1

NORMAL
FOCAL SLOW OR LOW ABNORMALITY
SEIZURE
GENERALIZED SLOW OR LOW ABNORMALITY
COMBINED ABNORMALITY

The term SLOW in slow abnormality refers to slower than normal average frequencies. The term LOW in low abnormality refers to lower than normal amplitude of EEG activity.

Figure 10:
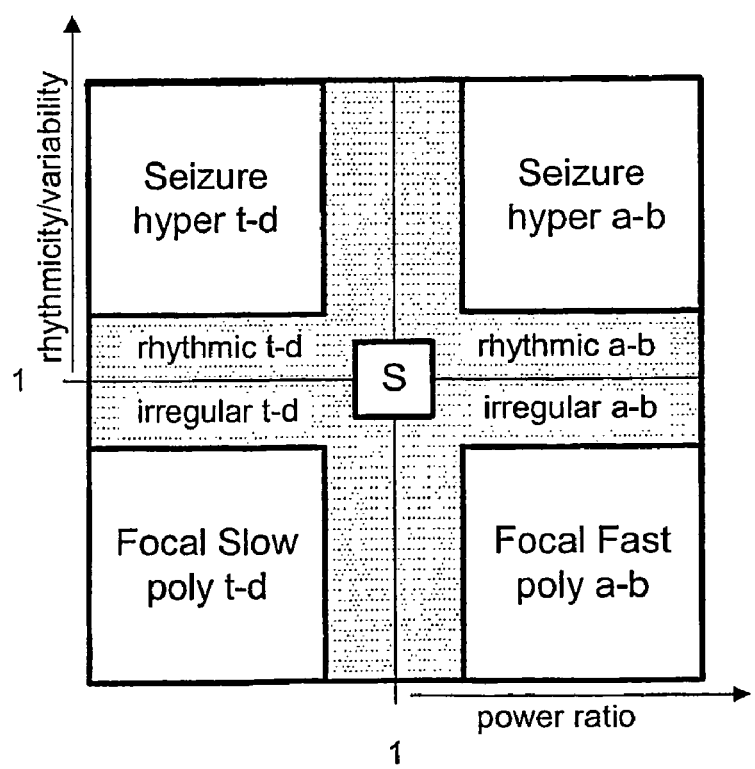
FIG. 10 is an illustrative logic diagram showing an x-y plot for QEEG analysis.

The AECS categories may then be correlated to a plot of the rhythmicity/variability value (as found using the methods described) versus the alpha-beta/theta-delta power ratio, as shown in FIG. 10. This logic diagram can also be used as a display template, as explained below.

The AECS categories have well-established correlations with specific types of brain dysfunction, which commonly occur in acute brain injuries and require urgent medical attention. For example, FOCAL SLOW ABNORMALITY indicates a localized structural abnormality of the brain, such as a stroke or hemorrhage. A GENERALIZED SLOW ABNORMALITY indicates a diffuse brain disturbance due to lack of oxygen, glucose or to an overdose of drugs or medications. A COMBINED ABNORMALITY would be subcategorized as a combination of first through fourth category. For example, a brain trauma injury to the right side of the brain, which also produced seizures, could be communicated in text or visually as a "COMBINED ABNORMALITY-FS/SZ" (e.g., focal slow+seizure).

Each category of the AECS may be assigned a specific color code, sound, or text description. In such embodiment, the EEG acquisition unit is coupled to a display device which displays the designated color, and displays the textual name of the AECS category which is the best fit with the automated analysis of the patient's EEG activity during the real-time acquisition-analysis of the patient's EEG, using the rhythmicity/variability vs. power ratio classification. Additionally, optionally the display devices include a sound emitting device which emits the designated sound of the AECS category which is the best fit.

In the FIG. 10, hyper-rhythmic theta-delta is associated with the upper left area, hyper-rhythmic alpha-beta is associated with the upper right area, polymorphic theta-delta is associated with the lower left area, and polymorphic alpha-beta is associated with the lower right area. The cross-like central area is a normal range, moving towards rhythmicity or irregularity as it nears one of the outer quadrants.

Figure 15:
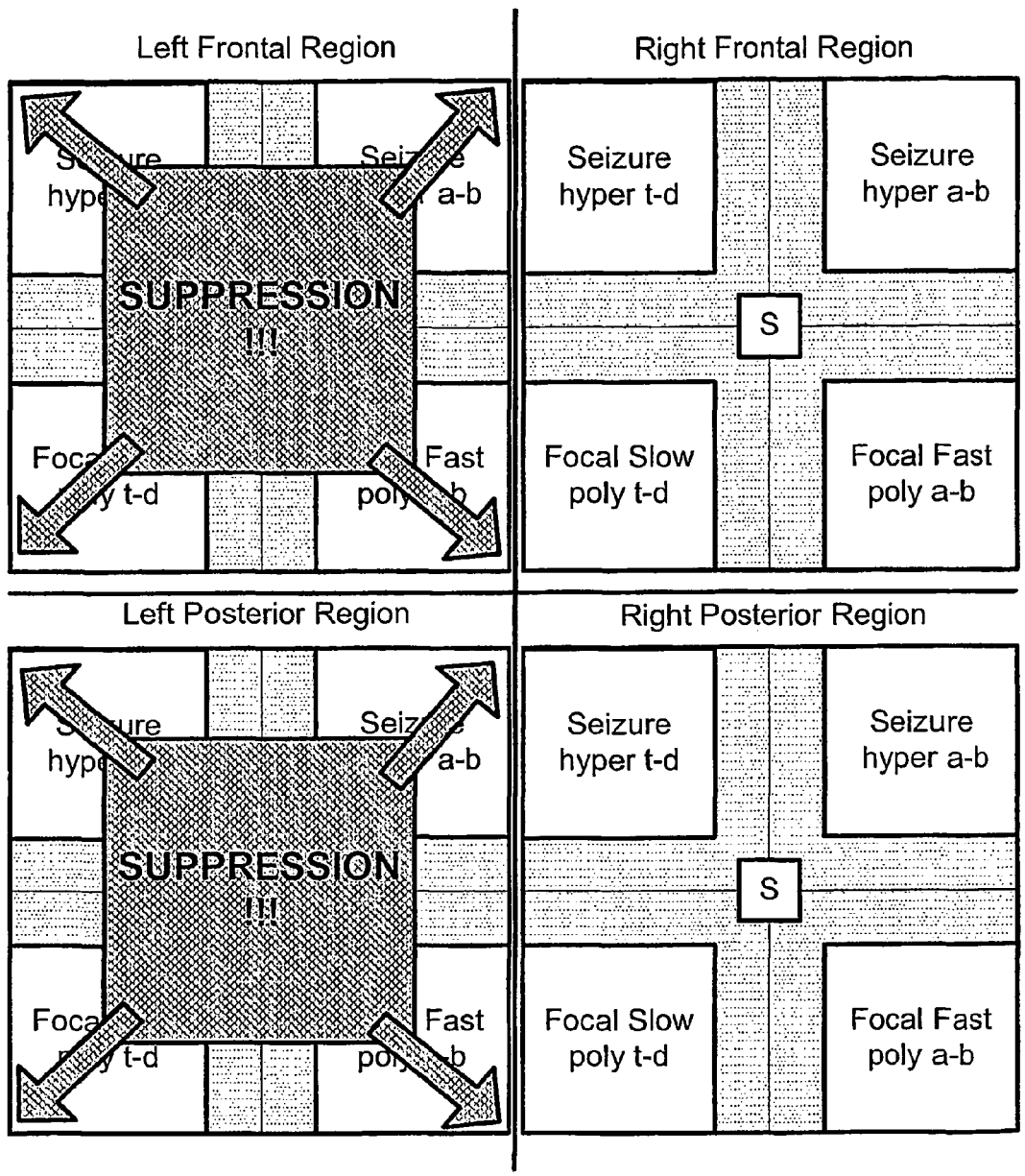
FIG. 15 is the logic diagram of FIG. 11 used in the system of FIG. 1.

It is also important to monitor the total power, the alpha-beta+theta-delta power, for occurrence of suppression of brain activity. In this embodiment, if the total power falls towards zero an alert mechanism triggers. This may be performed by indicia in the central area, marked by an "S" in FIG. 10, which in case of suppression can be made to expand in size and change color to draw operator attention to the suppression. An example is shown in FIG. 15. Other alert mechanisms will also work.

In a different embodiment, the EEG acquisition unit 18 includes a fourth memory 38 for storing an Auto EEG clinical correlation menu (not shown), which is a visual informational-cueing device to aide the operator in selecting the most appropriate clinical correlate of the AECS in the particular clinical context of the patient's ABI.

Figure 11:
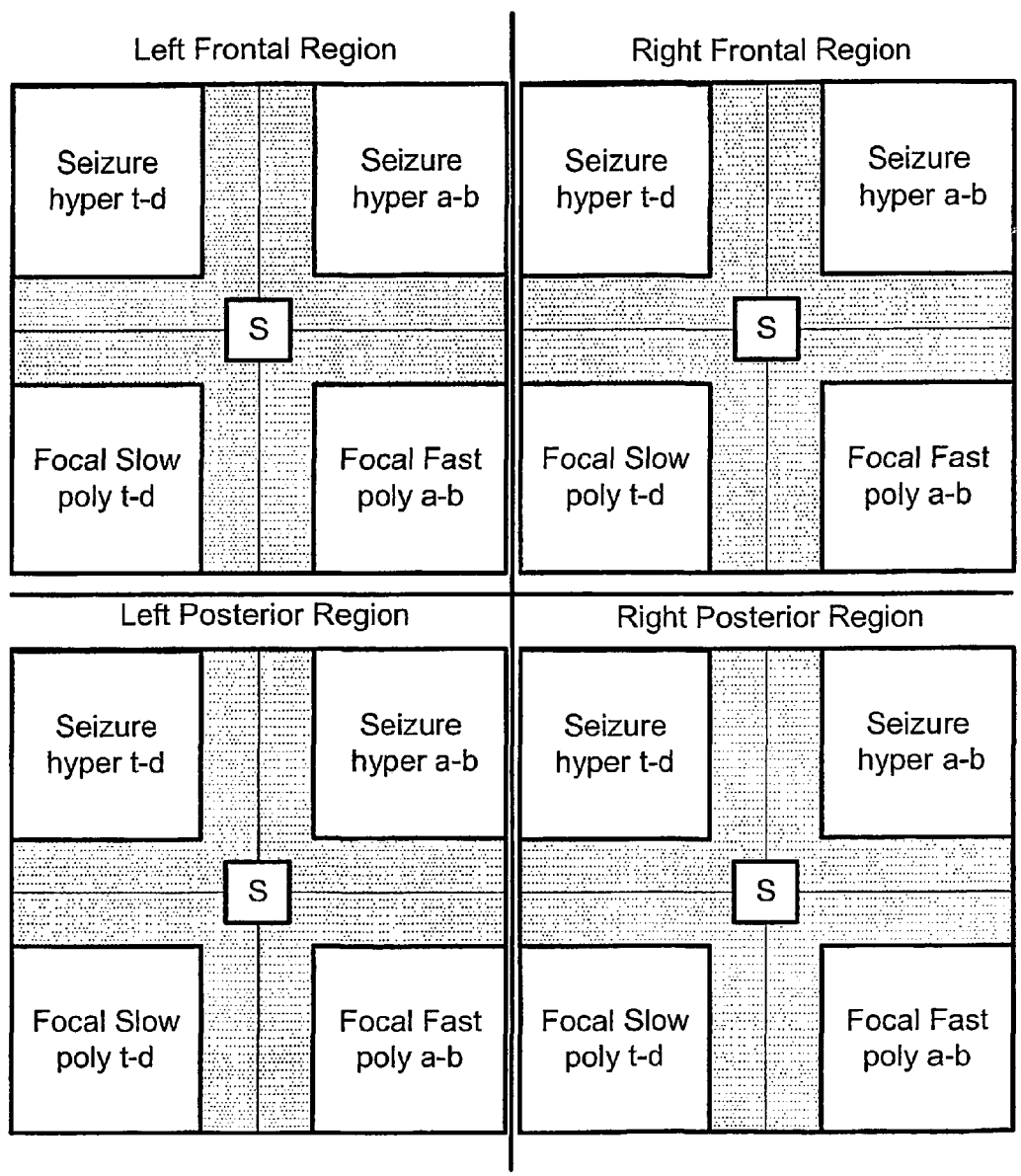
FIG. 11 is the logic diagram of FIG. 10 illustrating four quadrants of QEEG analysis.

In another embodiment, the brain can be divided into quadrants for the purpose of localizing EEG activity from scalp electrodes. Optionally, four separate quadrants can be used to represent different regions of the brain. FIG. 11 illustrates four quadrants of QEEG analysis using the logic diagram of FIG. 10, which reflect underlying real time EEG activity from respective regions of the brain to promote localization. This could readily be adapted to use on display 26. Alternatively, instead of displaying four quadrants a figure representing a patient's scalp may be displayed, the figure being divided to represent different regions of the brain.

Figure 12:
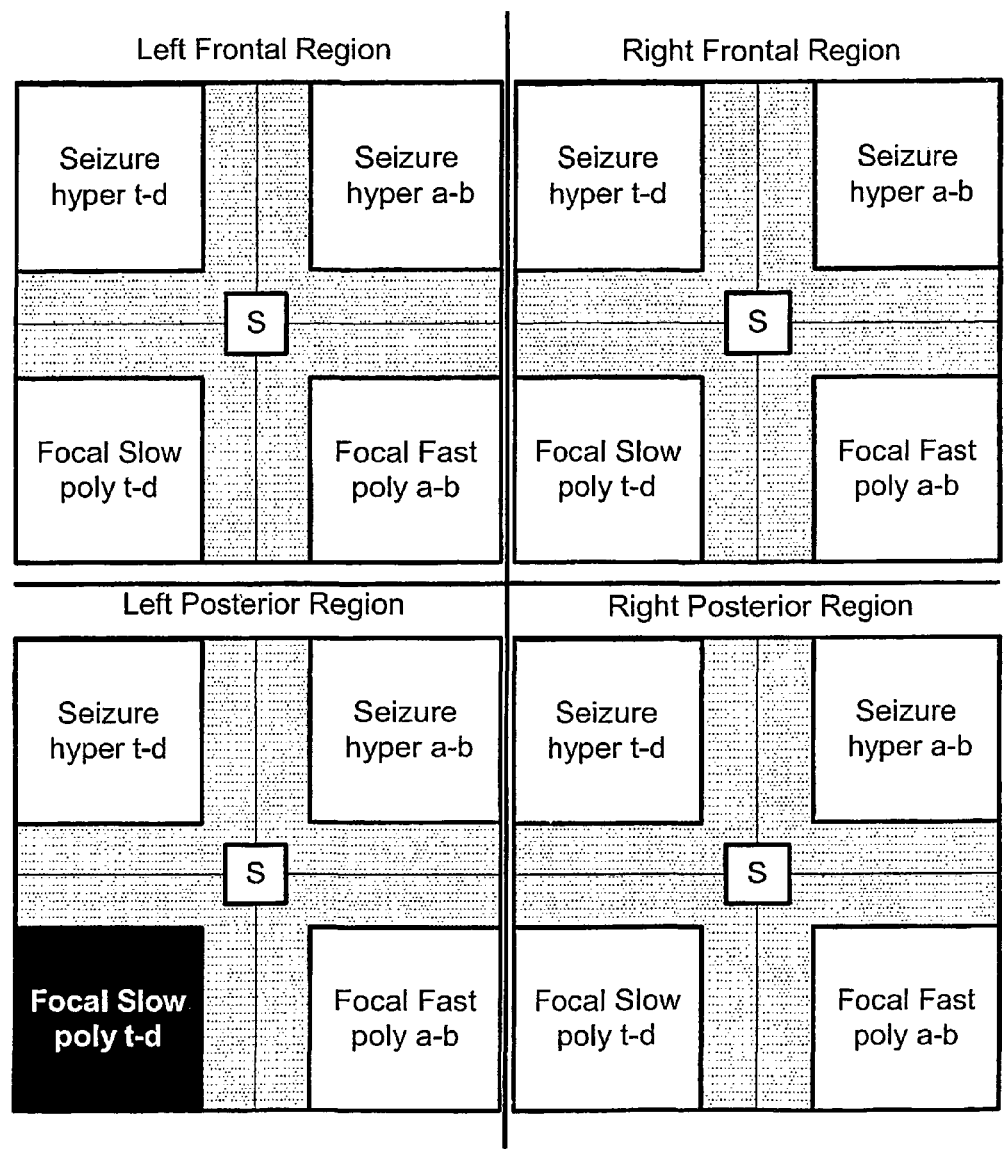
FIG. 12 is the logic diagram of FIG. 11 used in the system of FIG. 1.

FIG. 12 is a logic diagram as displayed on display 26 demonstrating the AutoEEG System 10 identifying an area of abnormally reduced rhythmicity and decreased power ratio localized to the left posterior region of the brain (left posterior parietal-occipital lobes). The program highlights the category of EEG abnormality and the region of localization. Accompanying audible cues, including verbal ones, can enhance the visual cues. This category of QEEG abnormality suggests a stroke, hemorrhage, traumatic injury, underlying tumor, or post-seizure metabolic fatigue (post-ictal state).

Figure 13:
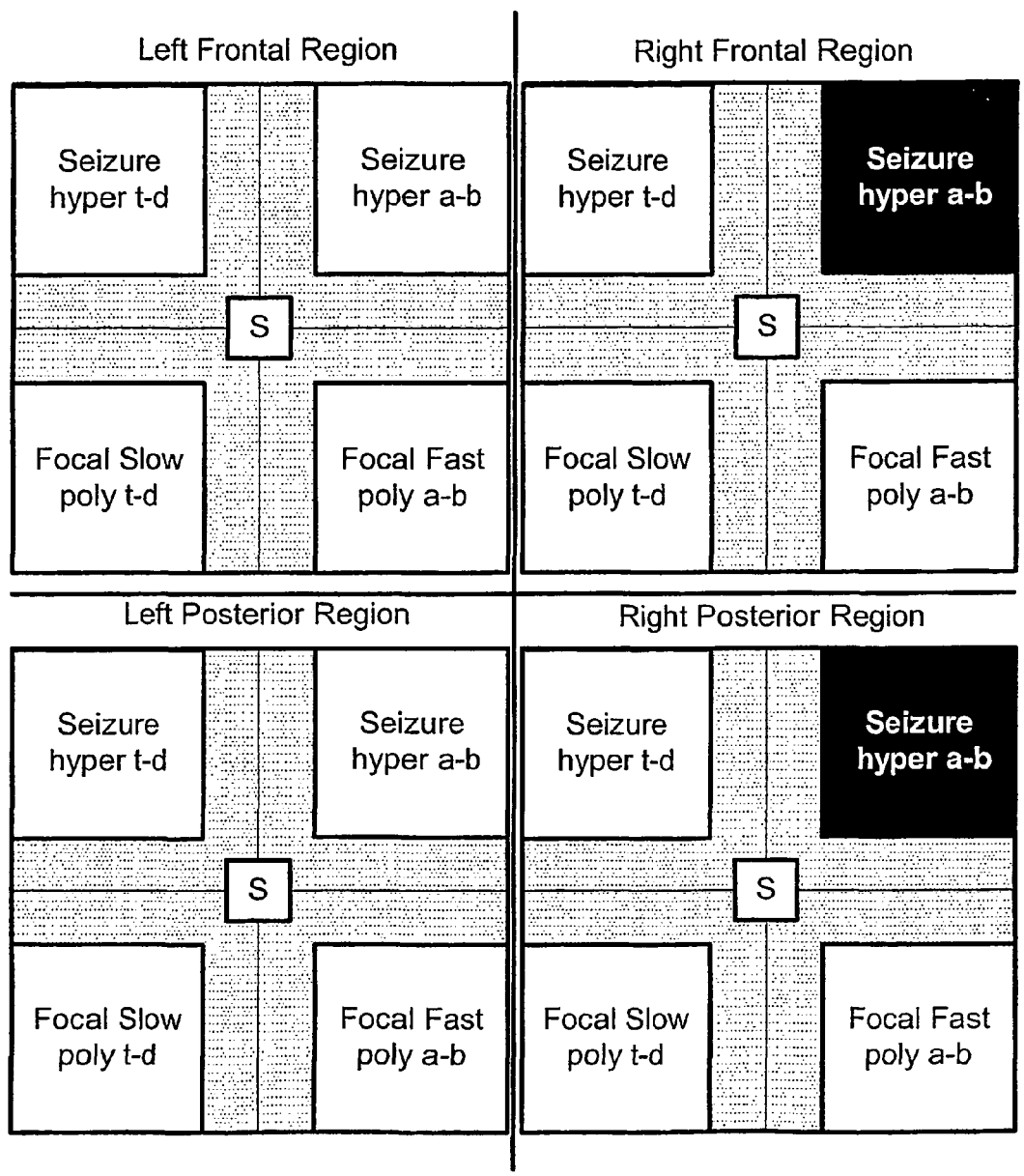
FIG. 13 is the logic diagram of FIG. 11 used in the system of FIG. 1.

FIG. 13 is a logic diagram as displayed on display 26 demonstrating the AutoEEG System 10 identifying abnormally increased rhythmicity and power of fast frequencies from both frontal and posterior quadrants of the right hemisphere. This indicates a focal seizure arising from the right hemisphere, but without a specific indication of whether the anterior or posterior regions are more involved. Accurate and timely emergency diagnosis, treatment and triage decisions can be made without this additional specificity.

Figure 14:
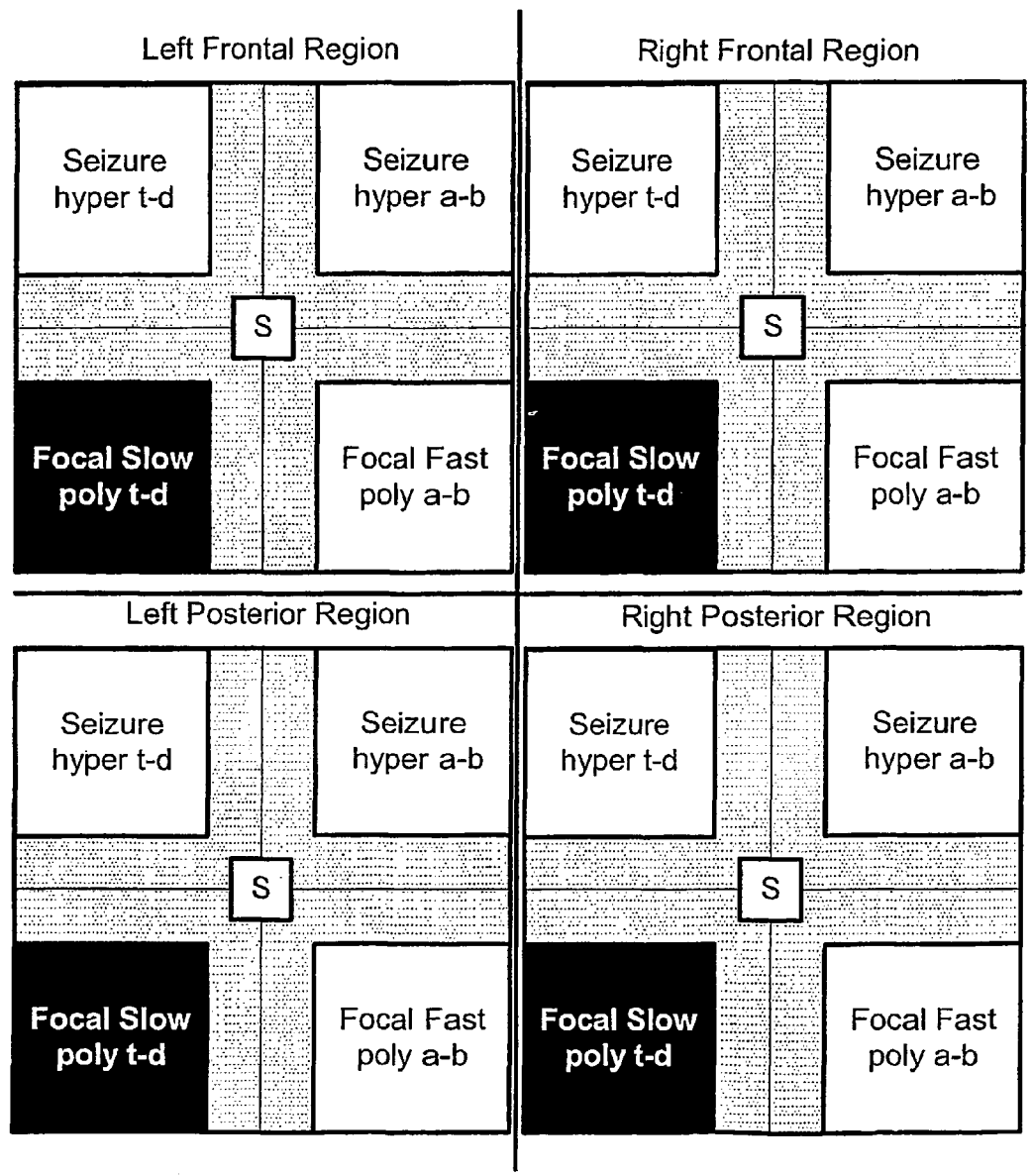
FIG. 14 is the logic diagram of FIG. 11 used in the system of FIG. 1.

FIG. 14 is a logic diagram as displayed on display 26 demonstrating the AutoEEG System 10 identifying an EEG pattern of generalized slow and irregular activity. This is characteristically seen in diffuse brain disturbances due to metabolic, toxic, and anoxic causes.

FIG. 15 is a logic diagram as displayed on display 26 demonstrating the AutoEEG System 10 indicating marked suppression of all frequencies in the left hemisphere. In this embodiment the central suppression alert has changed color and is expanding in size. This pattern is seen in large and severe strokes. It also occasionally occurs after severe focal seizures.

Optionally, the AutoEEG System 10 may include the option of human interpretation backup, because of system failure, unexpected complexity of the EEG or irresolvable artifact contamination, or other reasons, of transmitting the raw EEG data and/or any of the algorithmically processed data to a remote EEG expert reader via a telecommunications network.

In another separate alternative embodiment, the AutoEEG is exceptionally durable, sturdy, portable, and stable. Its electronic components can tolerate being in the "on" mode almost continuously to avoid time delays for "booting up" the system.

Figure 4:
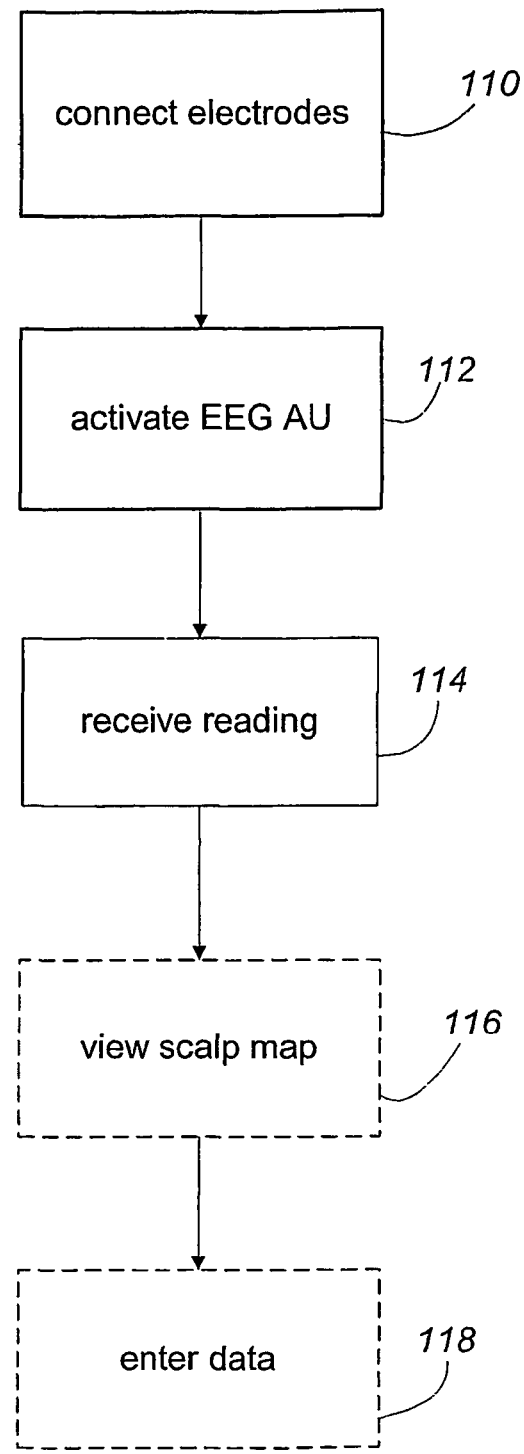
FIG. 4 is a flow diagram of a method for automated real time interpretation of brain waves in an acute brain injury of a patient under the control of a user.

FIG. 4 illustrates a method for automated real time interpretation of brain waves in an acute brain injury of a patient under the control of a user using AutoEEG system 10. In step 110 the user connects one or more than one electroencephalogram needle electrode from an electroencephalogram acquisition unit to a patient. Next, in step 112 the user activates the EEG AU and transmits digital electroencephalographic signals from the patient to the electroencephalogram acquisition unit. Preferably, upon being turned on, a window shown on the display device welcomes the user to the unit in a simple and graphically friendly and pleasing fashion. In step 114, the user receives a display of the EEG of the patient connected to the electroencephalogram acquisition unit display device and information automatically interpreting the meaning of the display. The EEG of the connected patent is displayed according to predetermined default parameters including time base, amplitude, sensitivity, low frequency filter, high frequency filter settings, and 60 Hz notch filter settings. In a further embodiment, these settings are not changeable or controllable by the on-site operator except by password access.

In an optional step 116, the user is presented with a window on the display device which shows a scalp map representing the positions of the EEG needle electrodes on the connected patient's head. These are color coded green or red to indicate acceptable (green) impedance range or unacceptable (red) impedance range. This display cues the operator about one or more specific electrodes and their positions, which may require manipulation to improve the quality of the recording. Optionally, the user may receive a request to enter the demographic data relating to the connected patient. Optionally, the EEG AU may allow the user to enter requested information by scanning bar-coded data belonging to the connected patient.

Optionally, in step 118 the user may receive a request to enter the necessary clinical information about the connected patient's condition, medications, and other relevant medical information required for clinical correlation of the EEG data.

Optionally, the information requested may be provided to the user in the form of pull-down menus from which the user selects the appropriate choices with a simple keystroke or mouse click.

In the foregoing specification, the invention has been described with reference to specific embodiments thereof It will, however, be evident that various modifications and changes may be made thereto without departing from the broader spirit and scope of the invention. The specification and drawings are, accordingly, to be regarded in an illustrative rather than a restrictive sense. It should be appreciated that the present invention should not be construed as limited by such embodiments, but rather construed according to the below claims.

What is claimed is:

1. A method for automated real time interpretation of brain waves in an acute brain injury of a patient, comprising:
    determining an alpha-beta/theta-delta power ratio for the brain waves; and
    correlating the brain wave power ratio and wave morphology.

2. A method for automated real time interpretation of brain waves in an acute brain injury of a patient, comprising:
    determining a brain wave morphology by measuring the rhythmicity and variability of the brain waves as a function of the slope of the brain waves' upstrokes, the area of the brain waves, and the synchronicity of the brain waves; and
    correlating a brain wave frequency power ratio and the brain wave morphology.

3. A method for automated real time interpretation of brain waves in an acute brain injury of a patient, comprising the steps of:
    a) acquiring electroencephalographic signals from the patient;
    b) selecting one or more than one of the acquired electroencephalographic signal for analysis;
    d) transforming the one or more than one selected electroencephalographic signal into one or more than one frequency component;
    e) calculating a power ratio for each of the one or more than one selected electroencephalographic signal, wherein the power ratio is an alpha-beta/theta-delta power ratio;
    f) accessing a reference database storing reference power ratios calculated from normal brain wave activity data;
    g) comparing the one or more than one calculated power ratio to the reference power ratios to determine whether the one or more than one calculated power ratio is abnormally high or low;
    h) interpreting the one or more than one selected electroencephalographic signal based upon the comparison of the one or more than one calculated power ratio to the reference power ratios; and
    i) communicating the interpretation of the selected electroencephalographic signals as the interpretation of the acquired electroencephalographic signals.

4. The method of claim 3, further comprising the step of measuring the wave morphology of the one or more than one selected electroencephalographic signal, and wherein the interpreting step further comprises consideration of the measured wave morphology.

5. The method of claim 3, wherein the reference database further comprises classification data correlating acute brain injury electroencephalographic categories with specific types of brain dysfunction, wherein the method further comprises the step of classifying the one or more than one compared power ratio into one or more than one of the acute brain injury electroencephalographic categories, and wherein the communicating step further comprises communicating the classification.

6. The method of claim 3, wherein the step of comparing further comprises determining the spatial distribution of any abnormality.

7. The method of claim 3, wherein the communicating step further comprises displaying a quadrant schematic representation for communicating the interpretation of the electroencephalographic signals.

8. A method for automated real time interpretation of brain waves in an acute brain injury of a patient, comprising the steps of:
    a) acquiring electroencephalographic signals from the patient;
    b) selecting one or more than one of the acquired electroencephalographic signal for analysis;
    d) transforming the one or more than one selected electroencephalographic signal into one or more than one frequency component;
    e) calculating a power ratio for each of the one or more than one selected electroencephalographic signal;
    f) accessing a reference database storing reference power ratios calculated from normal brain wave activity data;
    g) comparing the one or more than one calculated power ratio to the reference power ratios to determine whether the one or more than one calculated power ratio is abnormally high or low;
    h) measuring wave morphology of the one or more than one selected electroencephalographic signal, wherein wave morphology is determined by a measure of the rhythmicity and variability of the brain wave, as a function of the slope of the brain wave upstroke, the area of the brain wave, and the synchronicity of the brain wave;

i) interpreting the one or more than one selected electroencephalographic signal based upon the comparison of the one or more than one calculated power ratio to the reference power ratios and upon consideration of the measured wave morphology; and j) communicating the interpretation of the selected electroencephalographic signals as the interpretation of the acquired electroencephalographic signals.

9. The method of claim 8, wherein the reference database further comprises classification data correlating acute brain injury electroencephalographic categories with specific types of brain dysfunction, wherein the method further comprises the step of classifying the one or more than one compared power ratio into one or more than one of the acute brain injury electroencephalographic categories, and wherein the communicating step further comprises communicating the classification.

10. The method of claim 8, wherein the step of comparing further comprises determining the spatial distribution of any abnormality.

11. The method of claim 8, wherein the communicating step further comprises displaying a quadrant schematic representation for communicating the interpretation of the electroencephalographic signals.

12. A system for automated real time interpretation of brain waves in acute brain injuries in a patient, comprising:
a) a central processing unit;
b) an electroencephalogram acquisition unit coupled to the central processing unit having a first port for receiving electroencephalographic signals;
c) a reference database coupled to the central processing unit for storing one or more than one reference power ratio calculated from normal brain wave activity;
d) a first memory coupled to the central processing unit for storing a quantitative electroencephalogram analysis program, the quantitative electroencephalogram analysis program comprising:
a transform module for transforming acquired electroencephalographic signals into frequency components;
a calculation module for calculating a power ratio from the frequency components, wherein the calculated power ratio is an alpha-beta/theta-delta power ratio;
a classification module for comparing the calculated power ratio to reference data and classifying the acquired electroencephalographic signals; and
e) a display device for communicating the classification of the acquired electroencephalographic signals.

13. The system of claim 12, wherein the reference database further comprises classification data correlating acute brain injury electroencephalographic categories with specific types of brain dysfunction, the classification module is further for classifying the calculated power ratio into one or more than one of the acute brain injury electroencephalographic categories, and the display device is further for communicating the classification.

14. The system of claim 12, wherein the classification module is an artificial neural network.

15. The system of claim 12, further comprising a second memory coupled to the central processing unit for storing an artifact pattern recognition program for minimizing artifact contamination of received digital electroencephalographic signals.

16. A system for automated real time interpretation of brain waves in acute brain injuries in a patient, comprising:
a) a central processing unit;
b) an electroencephalogram acquisition unit coupled to the central processing unit having a first port for receiving electroencephalographic signals;
c) a reference database coupled to the central processing unit for storing one or more than one reference power ratio calculated from normal brain wave activity;
d) a first memory coupled to the central processing unit for storing a quantitative electroencephalogram analysis program, the quantitative electroencephalogram analysis program comprising:
a transform module for transforming acquired electroencephalographic signals into frequency components;
a calculation module for calculating a power ratio from the frequency components, wherein the calculation module is further for calculating rhythmicity and variability of the brain wave, as a function of the slope of the brain wave upstroke, the area of the brain wave, and the synchronicity of the brain wave;
a classification module for comparing the calculated power ratio to reference data and classifying the acquired electroencephalographic signals; and
e) a display device for communicating the classification of the acquired electroencephalographic signals.

17. The system of claim 16, wherein the reference database further comprises classification data correlating acute brain injury electroencephalographic categories with specific types of brain dysfunction, the classification module is further for classifying the calculated power ratio into one or more than one of the acute brain injury electroencephalographic categories, and the display device is further for communicating the classification.

18. The system of claim 16, wherein the classification module is an artificial neural network.

19. The system of claim 16, further comprising a second memory coupled to the central processing unit for storing an artifact pattern recognition program for minimizing artifact contamination of received digital electroencephalographic signals.

20. A system for automated real time interpretation of brain waves in acute brain injuries in a patient, comprising:
a) means for processing electroencephalographic signals;
b) means for receiving electroencephalographic signals from the patient;
c) means for storing one or more than one reference power ratio calculated from normal brain wave activity;
d) means for storing a quantitative electroencephalogram analysis program, the quantitative electroencephalogram analysis program comprising:
means for transforming acquired electroencephalographic signals into frequency components;
means for calculating an alpha-beta/theta-delta power ratio from the frequency components;
means for comparing the calculated power ratio to reference data and classifying the acquired electroencephalographic signals; and
e) means for communicating the classification of the acquired electroencephalographic signals.

* * * * *